United States Patent [19]
Allen et al.

[11] Patent Number: 5,932,549
[45] Date of Patent: Aug. 3, 1999

[54] N-SUBSTITUTED GLUTAMIC ACID DERIVATIVES WITH INTERLEUKIN-1β CONVERTING ENZYME INHIBITORY ACTIVITY

[75] Inventors: Hamish John Allen; Subhashis Banerjee, both of Shrewsbury; Kenneth Dale Brady, Worcester, all of Mass.; John Cooke Hodges, Ann Arbor; Catherine Rose Kostlan, Saline, both of Mich.; Robert Vincent Talanian, Harvard, Mass.

[73] Assignees: Warner-Lambert Company, Morris Plains, N.J.; BASF Aktiengesellschaft, Ludwigshafen, Germany

[21] Appl. No.: 09/067,053

[22] Filed: Apr. 27, 1998

Related U.S. Application Data

[62] Division of application No. 08/700,716, Aug. 13, 1996, Pat. No. 5,744,451.
[60] Provisional application No. 60/003,728, Sep. 14, 1995.

[51] Int. Cl.$^6$ ............ A61K 38/05; A61K 38/06; A61K 38/09
[52] U.S. Cl. ............ 514/18; 530/330; 530/331
[58] Field of Search ............ 514/18; 530/330, 530/331

[56] References Cited

FOREIGN PATENT DOCUMENTS

| 95/33751 | 12/1995 | WIPO . |
| 95/35308 | 12/1995 | WIPO . |
| 96/30395 | 10/1996 | WIPO . |

*Primary Examiner*—Cecilia J. Tsang
*Assistant Examiner*—Michael Borin
*Attorney, Agent, or Firm*—Elizabeth M. Anderson

[57] ABSTRACT

The present invention relates to N-substituted derivatives of glutamic acid of pharmaceutical interest, to pharmaceutical compositions which include compounds of the invention and pharmaceutically acceptable carriers, to methods of their preparation, and to their use in purification of interleukin-1β converting enzyme (ICE).

1 Claim, No Drawings

N-SUBSTITUTED GLUTAMIC ACID DERIVATIVES WITH INTERLEUKIN-1β CONVERTING ENZYME INHIBITORY ACTIVITY

This application is a divisional of application Ser. No. 08/700,716 filed Aug. 13, 1996, now allowed, as U.S. Pat. No. 5,744,451, which claims the benefit of Provisional application Ser. No. 60/003,728 filed Sep. 14, 1995, now abandoned.

BACKGROUND OF THE INVENTION

The present invention relates to N-substituted derivatives of glutamic acid of pharmaceutical interest, to pharmaceutical compositions which include compounds of the invention and pharmaceutically acceptable carriers, to methods of their preparation, and to their use in purification of interleukin-1β converting enzyme (ICE). The novel compounds of the present invention are inhibitors of ICE and hence are useful in controlling human disorders associated with generation of interleukin-1β (IL-1β), including but not limited to rheumatoid arthritis, inflammatory bowel disease, stroke, Alzheimer's disease, septic shock, and acute myelogenous leukemia.

ICE acts on pro-interleukin-1β (pro-IL-1β) to generate interleukin-1β (IL-1β) which is an inflammatory cytokine. Cleavage occurs between aspartate 116 and alanine 117 of pro-IL-1β. The substrate specificity of ICE has been studied by P. R. Sleath, et al., in *J. Biological Chem.*, 1990;265:14526–14528 and by D. K. Miller, et al., in *Ann. NY Acad. Sci.*, 1993;696:133–48, who found ICE to be highly specific for aspartic acid residues at the P-1 position. Substitution of even highly similar amino acids such as glutamate or asparagine for aspartic acid at the P-1 position of decapeptides which span the ICE cleavage site in pro-IL-1β were found to reduce the rate of cleavage to less than five percent of the native decapeptide with aspartic acid at P-1. This high substrate specificity allows ICE to recognize and cleave only pro-IL-1β in vivo and hence inhibition of ICE would reduce or eliminate inflammatory reactions associated with excess ICE activity by preventing the formation of IL—β. Conditions associated with excess ICE activity may include, but are not limited to joint inflammation such as in rheumatoid arthritis, gastrointestinal inflammation such as with inflammatory bowel disease, neuroinflammatory disorders such as seen in stroke and Alzheimer's disease, septic shock, and cancerous diseases such as acute myelogenous leukemia. ICE inhibitors have potential therapeutic utility in such conditions.

Many peptidic inhibitors of ICE have been described in the literature including tetrapeptide aldehydes such as Ac-Tyr-Val-Ala-Asp[CHO] by SEQ ID NO.1 K. T. Chapman in *Bioorganic & Medicinal Chemistry Letters*, 1992;2:613–618, tripeptide aldehydes and derivatives such as Cbz-Val-Ala-Asp[CHO] by T. L. Graybill, et al., in *Int. J. Peptide Protein Res.*, 1994;44:173–182, peptidic acyloxymethyl ketone derivatives by R. E. Dolle, et al., in *J. Medicinal Chemistry*, 1994;37:563–564 and by C. V. C. Prasad, et al., in *Bioorganic & Medicinal Chemistry Letters*, 1995;5:315–318, and N-acyl-aspartic acid ketones by A. M. M. Mjalli, et al., in *Bioorganic & Medicinal Chemistry Letters*, 1995;5:1405–1408. In accordance with the substrate specificity of ICE, these previous disclosures focus on derivatives of aspartic acid as the preferred P-1 substituent. In the acyloxymethyl ketone papers by Dolle and Prasad, direct comparison of an acyloxymethyl ketone derived from aspartic acid to a similar compound derived from glutamic acid showed that, for ICE, the glutamic acid derived compound was "devoid of enzyme affinity" (quote from Dolle, et al., paper).

EP 0519748A discloses peptidyl derivatives as inhibitors of interleukin-1β converting enzyme.

EP 0529713A discloses an affinity chromatography matrix useful in purifying interleukin-1β converting enzyme.

EP 0547699A discloses peptidyl derivatives as inhibitors of interleukin-1β converting enzyme.

However, the compounds disclosed in the above references do not disclose or suggest the ICE inhibitory activity of the compounds described hereinafter. On the contrary, they suggest that compounds of the present invention would be unlikely to contain significant ICE inhibitory activity.

SUMMARY OF THE INVENTION

One embodiment of the present invention is a compound of Formula I or a pharmaceutically acceptable

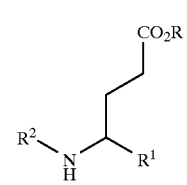

salt thereof wherein:

R is H, $CH_3$, $C_2H_5$, or $CH_2O$-alkyl;

$R^1$ is CHO, $COCH_3$, $COCF_3$, $CH(OCH_3)_2$, or CN; and $R^2$ is a tripeptide of the formula

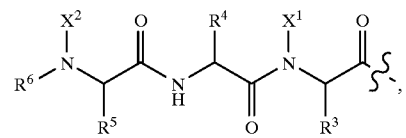

a dipeptide of the formula

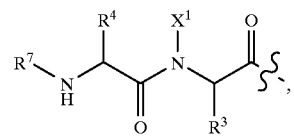

an amino acid derivative of the formula

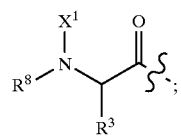

or an amide, carbamate, urea, or sulfonamide of the formula $R^8$.

According to the description above:

$R^3$ and $R^4$ are each independently H, $CH_3$, $C_2H_5$, n—$C_3H_7$, $CH(CH_3)_2$, n—$C_4H_9$, $CH_2CH(CH_3)_2$, $CH(CH_3)C_2H_5$, $CH_2OH$, $CH_2SH$, $CH_2CH_2OH$, $CH_2CH_2SCH_3$, $CH(OH)CH_3$, $CH_2CH=CH_2$,

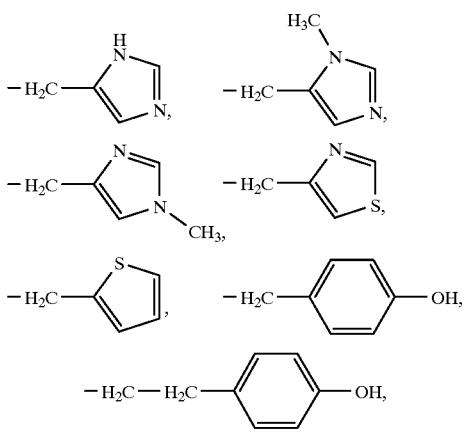

CH₂Ph, CH₂CH₂Ph, (CH₂)₃NH₂, (CH₂)₄NH₂, (CH₂)₃NHCOCH₃, (CH₂)₄NHCOCH₃, (CH₂)₃NHCOPh, (CH₂)₄NHCOPh, (CH₂)₃NHCO₂CH₂ph, (CH₂)₄NHCO₂CH₂Ph, CH₂CH₂CO₂H, CH₂CH₂CONH₂,

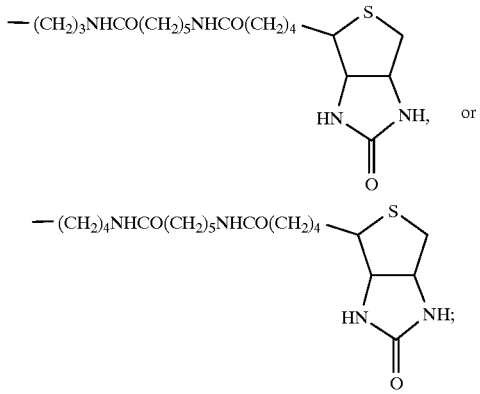

$X^1$ and $X^2$ are each independently H, or CH₃;

$R^5$ is CH₂Ph, CH₂CH₂Ph, CH₂(4-HO-Ph), CH₂CH₂(4-HO-Ph), CH₂-cyclohexyl, CH₂CH₂-cyclohexyl, CH₂CH(CH₃)₂, CHCH₂-(2-naphthyl), or CH₂-(3-indolyl);

$R^6$ is CH₃CO, CH₃CH₂CO, CH₃SO₂, CH₃CH₂SO₂, or

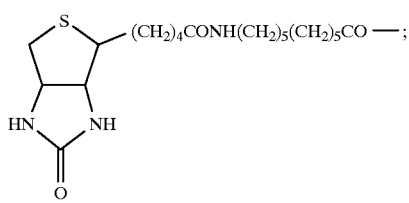

$R^7$ is PhCH₂OCO, PhCH₂CH₂OCO, PhCH₂CH₂CO, Ph(CH₂)₃CO, PhCH₂NHCO, PhCH₂CH₂NHCO, (2-naphthyl)—CH₂CO, or (2-naphthyl)—CH₂CH₂CO; and $R^8$ is $R^9$CO, $R^9$OCO, $R^9$NHCO, or $R^9$SO₂ where $R^9$ is alkyl, alkenyl, aryl, arylalkyl, cycloalkyl, (cycloalkyl)alkyl, heterocycle, or (heterocycle)alkyl.

A second embodiment of the invention is a method for preparation of compounds of Formula I by multiple, simultaneous synthesis. Additional embodiments of the invention are the uses of compounds of Formula I in treating rheumatoid arthritis, inflammatory bowel disease, stroke, Alzheimer's disease, septic shock, and acute myelogenous leukemia. A final embodiment of the invention is the use of selected compounds of Formula I in the purification of ICE.

DETAILED DESCRIPTION OF THE INVENTION

The following definitions apply to terms used in the description of Formula I:

"Alkyl" is a straight or branched chain of eight or fewer carbon atoms that is unsubstituted or substituted by one or two functional groups selected from OH, NH₂, OCH₃, CO₂H, CO₂CH₃, CONH₂, =O, or CN.

"Alkenyl" is an alkyl group defined as above with one or two carbon double bonds.

"Cycloalkyl" is a ring of from three to eight carbon atoms that is unsubstituted or substituted by one or two functional groups selected from OH, NH₂, OCH₃, CO₂H, CO₂CH₃, CONH₂, =O, or CN.

"(Cycloalkyl)alkyl" is a straight chain of from one to five carbon atoms which is substituted by a cycloalkyl group as described above.

"Aryl" is a benzene or naphthyl ring that is unsubstituted or substituted by one to three functional groups selected from CH₃, CF₃, F, Cl, Br, I, NO₂, OH, NH₂, OCH₃, CHO, CH₂OH, CO₂H, CO₂CH₃, CONH₂, or CN.

"Arylalkyl" is a straight chain of from one to five carbon atoms which is substituted by an aryl group as describe above.

"Heterocycle" is an aliphatic or aromatic five or six membered ring, or by an aromatic 5,6-fused or 6,6-fused bicyclic ring bearing one to four atoms selected from N, O, or S. The rings are unsubstituted or substituted by one to three functional groups selected from CH₃, CF₃, F, Cl, Br, I, NO₂, OH, NH₂, OCH₃, CHO, CH₂OH, CO₂H, CO₂CH₃, CONH₂, or CN.

"(Heterocycle)alkyl" is a straight chain of from one to five carbon atoms which is substituted by a heterocycle group as described above.

"Pharmaceutically acceptable salts" is as described by S. M. Berge, et al., in *Journal of Pharmaceutical Science*, 1977;66:1–19:

a) Acid addition salts—derived from nontoxic inorganic acids such as hydrochloric, nitric, phosphoric, sulfuric, hydrobromic, hydroiodic, phosphorous, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids, and the like.

b) Base addition salts—derived from alkaline earth metals including sodium, potassium, magnesium, calcium, and the like, as well as from nontoxic organic amines such as N,N'-dibenzylethylenediamine, N-Methylglucamine, chloroprocaine, choline, diethanolamine, ethylenediamine, procaine, and the like.

Common abbreviations for natural amino acids, common protecting groups, common solvents, and common reagents are as accepted by the *Journal of Organic Chemistry*. Amino acid abbreviations beginning with a capital letter indicate the L-enantiomer and those beginning with a lower case letter indicate the D-enantiomer, e.g., Phe (-phenylalanine) and phe (D-Phenylalanine). Other abbreviations include: Aha (L-6-aminohexanoic acid), hPhe (L-homophenylalanine), hTyr (L-homotyrosine), Cha (L-cyclohexylalanine), hCha (L-homocyclohexylalanine), Nle (L-butylglycine, also known as L-norleucine), Glu[CHO] (4-amino-4-formylbutanoic acid), Glu[CN] (4-amino-4-cyano-butanoic acid), DCC (dicyclohexylcarbodiimide), DIC (diisopropylcarbodiimide), EDAC (ethyldimethylaminopropylcarbodiimide hydrochloride), HOBT (1-hydroxybenzotriazole hydrate), AMC (7-amino-4-methylcoumarin), MBHA resin (methylbenzhydrylamine resin), BOP reagent (Benzotriazol-1-yloxy-tris (dimethylamino)-phosphonium hexafluorophosphate.

Compounds of the invention contain one or more chiral centers. Structures and compound names lacking a specific stereochemical definition define all possible stereoisomers.

Preferred compounds of the invention are those of Formula I wherein:

$R$ is H, $CH_3$, or $CH_2O$-alkyl;

$R^1$ is CHO, or CN; and $R^2$ is a tripeptide of the formula

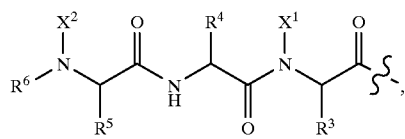

a dipeptide of the formula

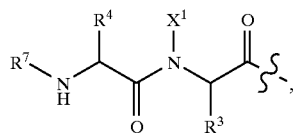

an amino acid derivative of the formula

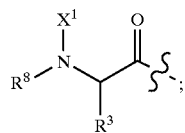

or an amide, carbamate, urea, or sulfonamide of the formula $R^8$.

According to the preferred description above:

$R^3$ is $CH_3$, $C_2H_5$, n—$C_3H_7$, n—$C_4H_9$, $CH(CH_3)_2$, $CH_2CH_2CO_2H$, $CH_2CH_2CONH_2$, $(CH_2)_4NH_2$,

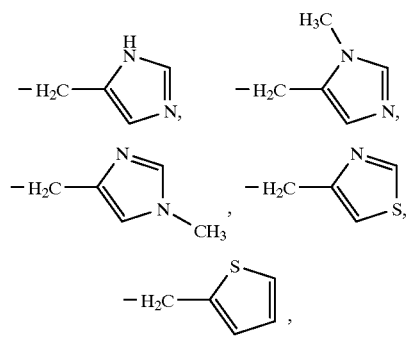

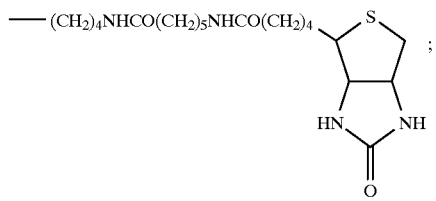

$R^4$ is n—$C_3H_7$, $CH(CH_3)_2$, n—$C_4H_9$, $CH_2CH(CH_3)_2$, $CH(CH_3)C_2H_5$, $CH(CH_3)OH$, $CH_2CH_2CO_2H$, $CH_2CH_2CONH_2$, or 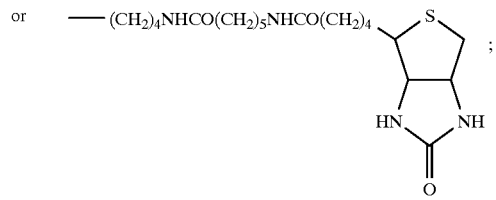

$X^1$ and $X^2$ are each independently H, or $CH_3$;

$R^5$ is $CH_2Ph$, $CH_2CH_2Ph$, $CH_2(4$-HO-Ph$)$, $CH_2CH_2(4$-HO-Ph$)$;

$R^6$ is $CH_3CO$, or

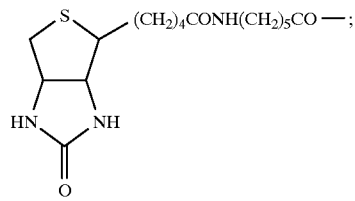

$R^7$ is $PhCH_2OCO$, $PhCH_2CH_2OCO$, $PhCH_2CH_2CO$, $Ph(CH_2)_3CO$, $PhCH_2NHCO$, $PhCH_2CH_2NHCO$, (2-naphthyl)—$CH_2CO$, or (2-naphthyl)—$CH_2CH_2CO$; and $R^8$ is $R^9CO$, $R^9OCO$, $R^9NHCO$, or $R^9SO_2$ where $R^9$ is aryl, arylalkyl, cycloalkyl, (cycloalkyl)alkyl, heterocycle, or (heterocycle)alkyl.

More preferred compounds of the invention are selected from the following list:

1) Ac-Tyr-Val-Ala-Glu[CHO] SEQ ID NO:2
2) Ac-Tyr-Nle-Ala-Glu[CHO] SEQ ID NO:3
3) Ac-hTyr-Val-Ala-Glu[CHO] SEQ ID NO:4
4) Ac-hTyr-Nle-Ala-Glu[CHO] SEQ ID NO:5
5) Ac-Tyr-Val-Ala-Glu[CN] SEQ ID NO:6
6) Ac-Tyr-Nle-Ala-Glu[CN] SEQ ID NO:7
7) Ac-hTyr-Val-Ala-Glu[CN] SEQ ID NO:8
8) Ac-hTyr-Nle-Ala-Glu[CN] SEQ ID NO:9
9) Cbz-Val-Ala-Glu[CHO]
10) Cbz-Nle-Ala-Glu[CHO]
11) Ph(CH$_2$)$_3$CO-Val-Ala-Glu[CHO]
12) Ph(CH$_2$)$_3$CO-Nle-Ala-Glu[CHO]
13) Cbz-Val-Ala-Glu[CN]
14) Cbz-Nle-Ala-Glu[CN]
15) Ph(CH$_2$)$_3$CO-Val-Ala-Glu[CN]
16) Ph(CH$_2$)$_3$CO-Nle-Ala-Glu[CN]
17) Ph(CH$_2$)$_5$CO-Ala-Glu[CHO]

18) Ph(CH$_2$)$_5$CO-Ala-Glu[CN]
19) Ac-Tyr-Glu-Val-Glu[CHO] SEQ ID NO:10
20) Ac-Tyr-Glu-Val-Glu[CN] SEQ ID NO:11
21) Ac-hTyr-Glu-Val-Glu[CHO] SEQ ID NO:12
22) Ac-hTyr-Glu-Val-Glu[CN] SEQ ID NO:13.

Any of the compounds of Formula I which contain a free amino group or a biotinoyl moiety may be utilized in the affinity purification of ICE. Preferred compounds for use in the affinity purification of ICE include compounds listed below:

1) Biotinoyl-Aha-Tyr-Val-Ala-Glu[CHO] SEQ ID NO:14
2) Ac-Tyr-Val-Lys(Aha-Biotinoyl)-Glu[CHO] SEQ ID NO:15
3) Ac-Tyr-Lys(Aha-Biotinoyl)-Glu[CHO].

These compounds serve as affinity ligands. They are first completed to an immobilized avidin such as avidin-sepharose. A crude cell preparation is then equilibrated with the immobilized ligand and eluted with a suitable buffer to remove unbound cellular materials. The column-bound ICE is then equilibrated with an excess of soluble Ac-Tyr-Val-Ala-Glu[CHO] and the purified ICE is eluted from the column in an inhibited form.

Compounds of Formula I are valuable inhibitors of ICE as demonstrated by measurement of $K_i$ and $k_{on}$ against ICE using the protocol described herein. ICE (0.24 nM) is added to 400 $\mu$L of HGDE buffer (100 mM HEPES, 20% glycerol, 5 mM DTT, and 0.5 mM EDTA) containing 250 $\mu$M substrate (Ac-Tyr-Val-Ala-Asp-AMC SEQ ID NO:16; $K_m$=15 $\mu$M). Substrate hydrolysis is monitored by observing the fluorescence of released AMC using excitation at 380 nM and emission at 460 nM. After linearity of the assay is confirmed, a compound of Formula I is added to a final concentration of [I]=2 or 4 $\mu$M, resulting in slow progressive decrease in the rate of substrate hydrolysis, with steady-state inhibition being achieved. The progress curves are fit to the equation $F=F_0+Vf.t+(V_i-V_f)(1-\exp(-k_{obs}t))/k_{obs}$, where $F_0$ is the initial fluorescence, $V_i$ and $V_f$ are initial and final reaction velocities, and $k_{obs}$ is the pseudo first-order rate of inhibition. $K_i$ is calculated as $K_i=SPF.[I]V_f/(V_i-V_f)$, where the substrate protection factor (SPF) is $1+[S]/K_m=17.7$. $k_{on}$ is calculated as $SPF.k_{obs}/[I]$.

Using these methods compounds of the invention can be shown to have $K_i$ values in the range of 0.5 nM to 50 $\mu$M and $k_{on}$ values in the range of $1\times10^4$ to $1\times10^6$ $^{=l\ M-1}s^{-1}$ for inhibition of ICE. For example, one compound of the instant invention, Ac-Tyr-Val-Ala-Glu[CHO] SEQ ID NO:2, gave $K_i$=1.8 nM and $k_{on}$=17,250 M$^{-1}$s$^{-1}$. Similar measurements applied to the reference ICE inhibitor, Ac-Tyr-Val-Ala-Asp [CHO] SEQ ID NO:2 gave $K_i$=0.7 nM and $k_{on}$=3×10$^5$ M$^{-1}$s$^{-1}$. The fact that these two molecules give similar $K_i$ values is unexpected based on the prior art since comparable substrates with Asp and Glu in the P-1 position show Glu to be detrimental to cleavage (P. R. Sleath, et al., *J. Biological Chem.*, 1990;265:14526–14528 and D. K. Miller, et al., *Ann. NY Acad. Sci.*, 1993;696:133–148) and since other, structurally distinct inhibitors show a clear preference for Asp analogs over Glu analogs (R. E. Dolle, et al., *J. Medicinal Chemistry*, 1994;37:563–564 and C. V. C. Prasad, et al., *Bioorganic & Medicinal Chemistry Letters*, 1995;5:315–318).

Further evidence that compounds of Formula I are valuable inhibitors of ICE is provided by their ability to inhibit IL-1β production in human peripheral blood mononuclear cells (PBMCs) as described herein. PBMCs are isolated from heparinized blood by centrifugation over a ficoll cushion, then washed three times with phosphate-buffered saline. PBMCs are suspended in a medium containing RPMI 1640 with glutamine, penicillin, streptomycin and 2% human AB serum, then plated at 10$^6$ cells per well in 96-well flat bottom plates. PBMCs are stimulated overnight with 10 ng/mL of lipopolysaccharide (LPS, *E. Coli* strain 0111:B4; Calbiochem) in the presence or absence of a compound of Formula I. Medium is harvested and the level of mature IL-1β was determined using an ELISA kit from R & D Systems. Cells were cultured for an additional 4 hours in the presence of 3-(4,5-dimethylthiazol-2-yl)-2,5-diphenyltetrazolium bromide (MTT) to determine viability.

In this assay, the compound of Formula I, Ac-Tyr-Val-Ala-Glu[CHO], at a concentration of 100 $\mu$M, inhibited the production of mature IL-1β by 90% relative to the level from control PBMCs treated with LPS alone. Cell viability after treatment with 100 $\mu$M Ac-Tyr-Val-Ala-Glu[CHO] was >95% as measured by the MTT assay. In similar experiments, the reference ICE inhibitor, Ac-Tyr-Val-Ala-Asp[CHO], at a concentration of 100 $\mu$M, also inhibited the production of mature IL-1β by 90% relative to control.

Compounds of Formula I may be prepared as outlined in Schemes 1 and 2. Although these schemes indicate only a limited range of structures, the methods apply widely to analogous compounds of Formula I, given appropriate consideration to the protection and deprotection of reactive functional groups by methods that are standard to the art of organic chemistry.

According to Scheme 1, the synthesis starts from Nα-Fmoc-glutamic acid γ-t-butyl ester, 1, which is converted to a mixed anhydride by treatment with isobutylchloroformate and N-methylmorpholine and subsequently treated with O,N-dimethylamine to afford 2. Reduction of 2 with LAH in THF at −60° C., followed by a mild acid work-up affords the aldehyde 3 which is condensed with the semicarbazide, 4, to afford 5 and coupled to MBHA resin with the BOP reagent as described by A. M. Murphy, et al., in *J. Am. Chem. Soc.*, 1992;114:3156–3157 to afford 6. Other common polymeric supports and coupling strategies may also be utilized, including those where the semicarbazide moiety is attached directly to the polymer or extended from the polymer by alternate linking groups. The remainder of the synthesis involves the sequential removal of the Fmoc group under standard conditions, such as 50% piperidine, morpholine, or piperazine in DCM or DMF, affording 7. Peptide and amide bonds may be formed by reacting 7 with a carboxylic acid halide or a mixed anhydride and a tertiary amine acid scavenger or alternatively by combining 7 and a carboxylic acid or protected amino acid with a wide variety of coupling reagents that are standard to the art of peptide chemistry. Sulfonamides are similarly prepared by reacting 7 with a sulfonyl chloride and tertiary amine. Cleavage of the t-butyl ester in 8 by treatment with TFA in DCM gives 9 which is subsequently cleaved from the resin by treatment with formaldehyde and dilute HCl to afford 10, a compound of Formula I.

SCHEME 1
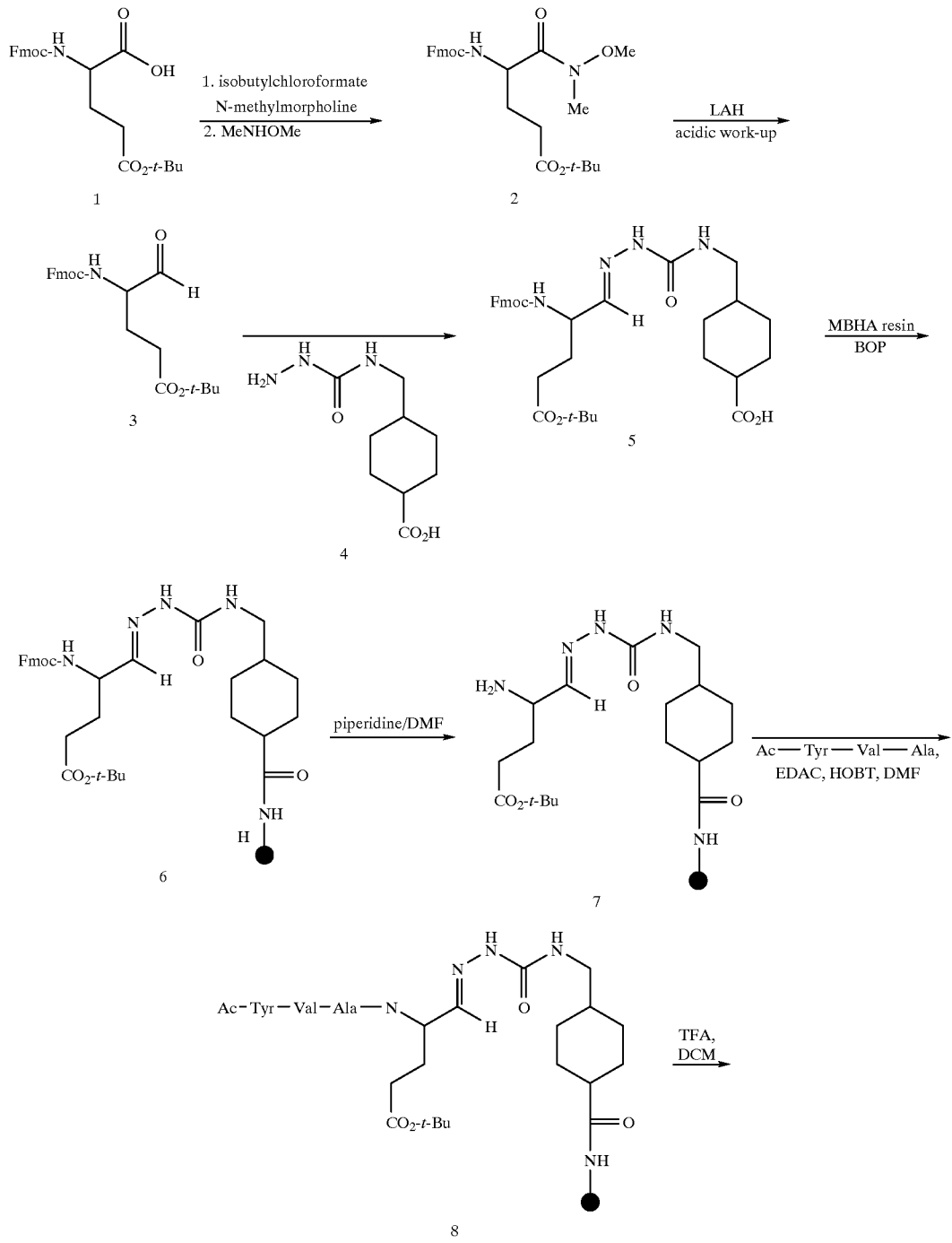

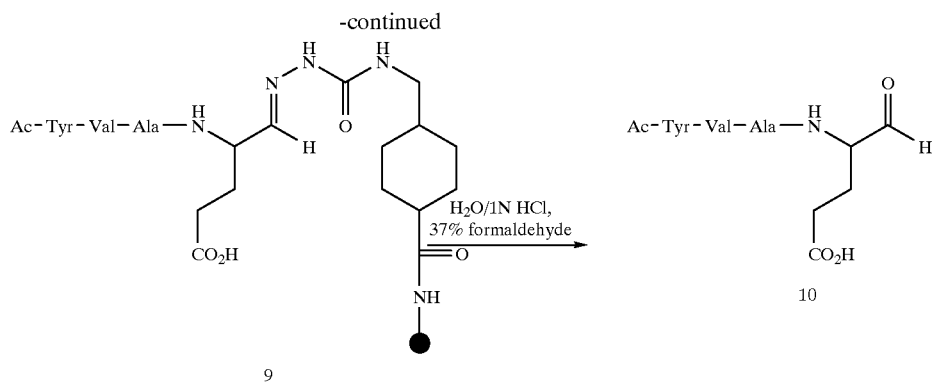

According to Scheme 2, the synthesis may also start with Nα-Fmoc-glutamic α-carboxamide γ-t-butyl ester, 11, which is dehydrated to the nitrile through the use of a carbodiimide reagent such as DCC, DIC, or EDAC to afford 12. Removal of the t-butyl ester protecting group with TFA in DCM gives 13 which is subsequently coupled to a solid support using a mixed anhydride method such as 2,6-dichlorobenzoyl chloride/pyridine or isobutylchloroformate/ N-methylmorpholine in DCM or dioxane solvent to afford 14. Solid supports are those common to solid phase peptide synthesis including, but not limited to, Wang resin, Merrifield resin, and 2-chlorotrityl resin. The remainder of the synthesis proceeds in a manner analogous to Scheme 1 to afford 17 which are compounds of Formula I.

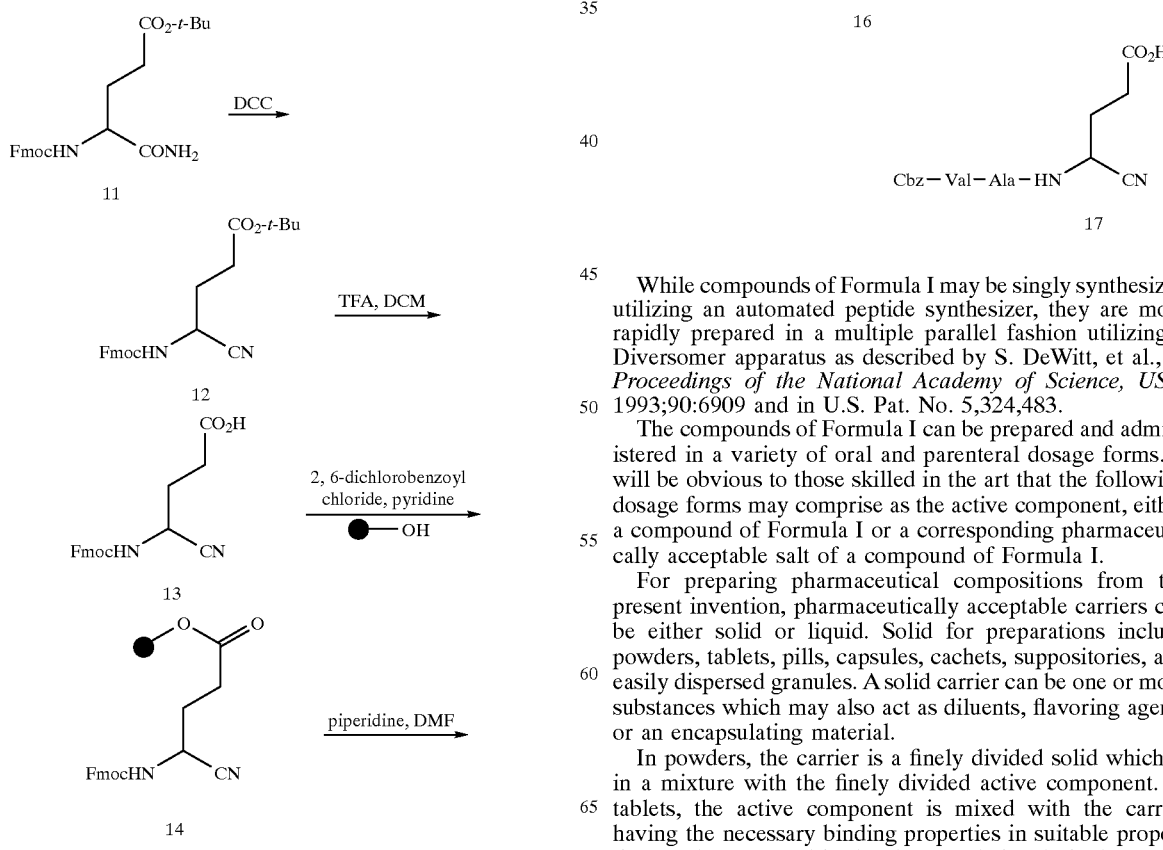

While compounds of Formula I may be singly synthesized utilizing an automated peptide synthesizer, they are more rapidly prepared in a multiple parallel fashion utilizing a Diversomer apparatus as described by S. DeWitt, et al., in *Proceedings of the National Academy of Science, USA*, 1993;90:6909 and in U.S. Pat. No. 5,324,483.

The compounds of Formula I can be prepared and administered in a variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the present invention, pharmaceutically acceptable carriers can be either solid or liquid. Solid for preparations include powders, tablets, pills, capsules, cachets, suppositories, and easily dispersed granules. A solid carrier can be one or more substances which may also act as diluents, flavoring agents or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with or without carriers which is surrounded by an encapsulating material. Similarly cachets and lozenges are included. Tablets, powders, capsules, pills, cachets, and lozenges can be used a solid dosage forms suitable for oral administration.

For preparing suppositories, a low melting wax, such as a mixture of fatty acid glycerides or cocoa butter, is first melted, and the active component is dispersed homogeneously therein. The molten, homogeneous mixture in then poured into convenient sized molds, allowed to cool, and thereby to solidify.

Liquid for preparations include solutions, suspensions, and emulsions. For parenteral injection, liquid preparations can be formulated, for example, by dissolution of the active component in water or in aqueous polyethylene glycol. For oral use, the active component may be dissolved in water or aqueous ethanol and adding suitable colorants, flavors, stabilizing and thickening agents as desired. Also for oral use, suspensions can be made by dispersing finely divided active component in water with viscous material, such as natural or synthetic gums, resins, methylcellulose, sodium carboxymethylcellulose, and other well-known suspending agents.

Also included are solid for preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be the capsules, tablet, cachet or lozenge itself, or it can be the appropriate number of any of these in packaged form. The quantity of active component in a unit dose preparation may be varied or adjusted from 0.1 mg to 100 mg according to the particular application and the potency of the active component. The composition can, if desired, also contain other compatible therapeutic agents.

In therapeutic use, the compounds utilized in the pharmaceutical method of this invention are administered at the initial dosage of about 0.1 mg to about 100 mg per kilogram daily. The dosage may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following examples illustrate methods for preparing intermediates and final products of the invention. They are not intended to limit the scope of the invention. Examples 1–6 describe in detail the methods outlined in Scheme 1.

EXAMPLE 1

Fmoc-Glu-(O-tBu)-N-Me(OMe) (1)

To a solution of Fmoc-glutamic acid γ-tBu ester (8.5 g, 20 mmol) and N-methylmorpholine (2.0 g, 20 mmol) in methylene chloride is added isobutylchloroformate (2.5 g, 20 mmol) at 0° C. under an atmosphere of dry nitrogen. The reaction mixture is stirred at 0° C. for 15 minutes followed by the dropwise addition of a solution of N-methyl-o-methylhydroxylamine hydrochloride (2.05 g, 21 mmol) and N-methylmorpholine (2 g, 20 mmol) in methylene chloride. The resulting solution is stirred at room temperature overnight and then evaporated under vacuum. The residue is partitioned between water and ethyl acetate and the organic layer washed successively with dilute aqueous sodium bicarbonate, 10% citric acid, and brine. The organic layer is dried over $MgSO_4$ and evaporated to give crude Fmoc-Glu-(O-tBu)-N-Me(OMe), 2, which is purified by flash chromatography.

EXAMPLE 2

Semicarbazone derivative (5)

To a solution of Fmoc-Glu-(O-tBu)-N-Me(OMe) (2.0 g, 4.3 mmol) in dry ether (450 mL) is added a solution of LAH (4.5 mL, 1M solution in THF) at −60° C. under an atmosphere of dry $N_2$. The reaction mixture is stirred at −60° C. for 15 minutes and quenched at −60° C. by the dropwise addition of an aqueous solution of $KHSO_4$ (2 g) in water (6 mL). The reaction mixture is allowed to warm to room temperature, treated with an excess of $MgSO_4$, and filtered through Celite. The filtrate is washed with 1N HCl, dried over $MgSO_4$, and evaporated to give the crude aldehyde, 3, which is not purified, but used directly in the next reaction to avoid racemization. The crude aldehyde is dissolved in a solution of the semicarbazide, 4, (1.5 g), in ethanol (50 mL). The reaction mixture is stirred at room temperature for 30 minutes, and the ethanol is evaporated. The residue is partitioned between methylene chloride, and the organic layer is dried over $MgSO_4$ and evaporated to give crude semicarbazide which is purified by flash chromatography.

EXAMPLE 3

Coupling of 5 to MBHA resin

Compound 5 is coupled to the resin using the BOP reagent as described by A. M. Murphy, et al. in *J. Am. Chem. Soc.*, 1992;114:3156–3157 to afford resin bound compound 6.

EXAMPLE 4

Removal of Fmoc protecting group

A mixture of 6 (100 mg) in DMF/piperidine was agitated for 1 hour at room temperature and filtered. The resin was successively washed with DMF, DCM, anhydrous EtOH, DCM, and DMF.

EXAMPLE 5

Acylation of 7

7 is added to a DMF solution containing a two-fold excess of Ac-Tyr-Val-Ala, EDAC and HOBT (in molar equivalent amounts). The resulting suspension is agitated for 4 hours, the resin is then filtered, rinsed with DMF, and subsequently resubjected to the coupling reaction. Filtration and sequential rinsing with DMF, DCM, anhydrous EtOH, DCM, and DMF affords 8.

EXAMPLE 6

Deprotection and Cleavage From the Resin 8 is treated with a 1:1 mixture TFA in DCM and agitated for 2 hours at room temperature to give 9 which was treated with 1N HCl and 37% formaldehyde according to the procedure described by A. M. Murphy, et al., in *J. Am. Chem. Soc.*, 1992;114:3156–3157 to liberate 10 from the resin. 10 is extracted into ethyl acetate, dried over $MgSO_4$, and evaporated.

We claim:

1. A method of inhibiting interleukin-1β converting enzyme activity in disorders such as; inflammatory bowel disease, stroke, Alzheimer's, septic shock and acute myelogenous leukemia in a human in need of said treatment comprising administering a compound of formula I or a pharmaceutically acceptable salt thereof wherein:

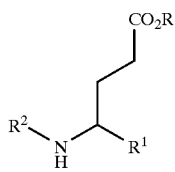

R is H;
$R^1$ is CHO, COCH$_3$, COCF$_3$, CH(OCH$_3$)$_2$ or CN; and
$R^2$ is a tripeptide of the formula

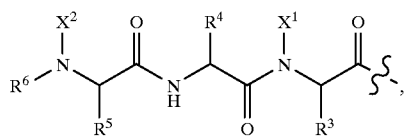

a dipeptide of the formula

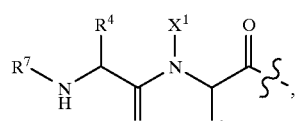

an amino acid derivative of the formula

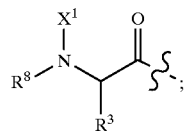

or an amide, urea, or sulfonamide of the formula $R^8$ and $R^2$ is amide when $R^1$ is not CN;

wherein $R^3$ and $R^4$ are each independently H, CH$_3$, C$_2$H$_5$, n—C$_3$H$_7$, CH(CH$_3$)$_2$, n—C$_4$H$_9$, CH$_2$CH(CH$_3$)$_2$, CH(CH$_3$)C$_2$H$_5$, CH$_2$OH, CH$_2$SH, CH$_2$CH$_2$OH, CH$_2$CH$_2$SCH$_3$, CH(OH)CH$_3$, CH$_2$CH=CH$_2$,

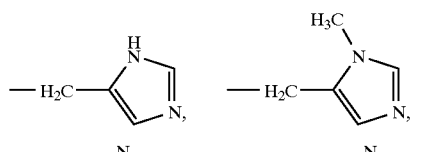

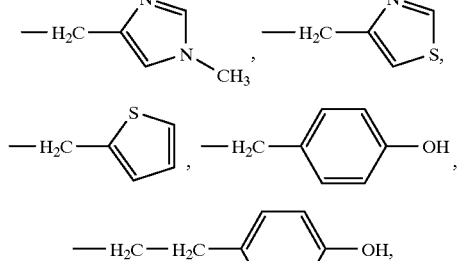

CH$_2$Ph, CH$_2$CH$_2$Ph, (CH$_2$)$_3$NH$_2$, (CH$_2$)$_4$NH$_2$, (CH$_2$)$_3$NHCOCH$_3$, (CH$_2$)$_4$NHCOCH$_3$, (CH$_2$)$_3$NHCOPh, (CH$_2$)$_4$NHCOPh, (CH$_2$)$_3$NHCO$_2$CH$_2$Ph, (CH$_2$)$_4$NHCO$_2$CH$_2$Ph, CH$_2$CH$_2$CO$_2$H, CH$_2$CH$_2$CONH$_2$.

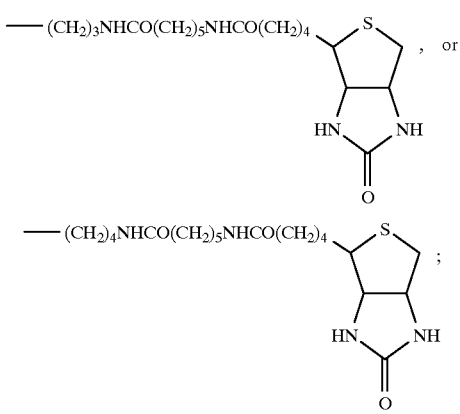

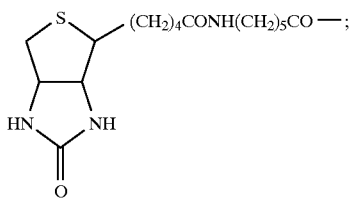

$X^1$ and $X^2$ are each independently H, or $CH_3$;

$R^5$ is $CH_2Ph$, $CH_2CH_2Ph$, $CH_2$(4-HO-Ph), $CH_2CH_2$(4-HO-Ph), $CH_2$-cyclohexyl, $CH_2CH_2$-cyclohexyl, $CH_2CH(CH_3)_2$, $CHCH_2$-(2-naphthyl), or $CH_2$-(3-indolyl);

$R^6$ is $CH_3CO$, $CH_3CH_2CO$, $CH_3SO_2$, $CH_3CH_2SO_2$, or $R^7$ is $PhCH_2OCO$, $PhCH_2CH_2OCO$, $PhCH_2CH_2CO$, $Ph(CH_2)_3CO$, $PhCH_2NHCO$, $PhCH_2CH_2NHCO$, (2-naphthyl)—$CH_2CO$, or (2-naphthyl)—$CH_2CH_2CO$; and $R^8$ is $R^9CO$, $R^9OCO$, $R^9NHCO$, or $R^9SO_2$ where $R^9$ is alkyl, alkenyl, aryl, arylalkyl, cycloalkyl, (cycloalkyl)alkyl heterocycle, or (heterocycle)alkyl wherein when $R^2$ is amide $R^9$ is not aryl.

* * * * *

```
                        SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Tyr Val Ala Asp
    1

(2) INFORMATION FOR SEQ ID NO:2:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Tyr Val Ala Glu
    1

(2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Tyr Xaa Ala Glu
    1

(2) INFORMATION FOR SEQ ID NO:4:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Xaa Val Ala Glu
    1

(2) INFORMATION FOR SEQ ID NO:5:
```

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:5:

Xaa Xaa Ala Glu
       1

(2) INFORMATION FOR SEQ ID NO:6:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Tyr Val Ala Glu
       1

(2) INFORMATION FOR SEQ ID NO:7:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

Tyr Xaa Ala Glu
       1

(2) INFORMATION FOR SEQ ID NO:8:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:8:

Xaa Val Ala Glu
       1

(2) INFORMATION FOR SEQ ID NO:9:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:9:

Xaa Xaa Ala Glu
       1

(2) INFORMATION FOR SEQ ID NO:10:

```
      (i) SEQUENCE CHARACTERISTICS:
          (A) LENGTH: 4 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:10:

Tyr Glu Val Glu
     1

(2) INFORMATION FOR SEQ ID NO:11:

(i) SEQUENCE CHARACTERISTICS:
          (A) LENGTH: 4 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:11:

Tyr Glu Val Glu
     1

(2) INFORMATION FOR SEQ ID NO:12:

(i) SEQUENCE CHARACTERISTICS:
          (A) LENGTH: 4 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:12:

Xaa Glu Val Glu
     1

(2) INFORMATION FOR SEQ ID NO:13:

(i) SEQUENCE CHARACTERISTICS:
          (A) LENGTH: 4 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:13:

Xaa Glu Val Glu
     1

(2) INFORMATION FOR SEQ ID NO:14:

(i) SEQUENCE CHARACTERISTICS:
          (A) LENGTH: 4 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:14:

Tyr Val Ala Glu
     1

(2) INFORMATION FOR SEQ ID NO:15:
```

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:15:

Tyr Val Xaa Glu
 1

(2) INFORMATION FOR SEQ ID NO:16:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:16:

Tyr Val Ala Asp